United States Patent [19]

Archer

[11] Patent Number: 4,539,412
[45] Date of Patent: Sep. 3, 1985

[54] 7-HYDROXYLUCANTHONE, 7-HYDROXHYCANTHONE AND THEIR ANALOGS

[75] Inventor: Sydney Archer, Delmar, N.Y.

[73] Assignee: Rensselaer Polytechnic Institute, Troy, N.Y.

[21] Appl. No.: 576,015

[22] Filed: Feb. 1, 1984

Related U.S. Application Data

[63] Continuation-in-part of Ser. No. 405,378, Jul. 8, 1982, abandoned, which is a continuation-in-part of Ser. No. 396,433, Aug. 5, 1982, abandoned.

[51] Int. Cl.$^3$ .................. C07D 311/86; C07D 335/16
[52] U.S. Cl. ........................................ 549/27; 544/145; 544/150; 544/375; 546/196; 546/202; 548/525; 549/392; 514/908
[58] Field of Search .................. 549/27, 392; 548/525; 546/202, 196; 544/145, 375, 150

[56] References Cited

U.S. PATENT DOCUMENTS

| | | | |
|---|---|---|---|
| 2,627,518 | 2/1953 | Archer | 549/27 X |
| 2,631,154 | 3/1953 | Archer | 549/392 |
| 2,653,949 | 9/1953 | Archer | 549/27 |
| 2,653,950 | 9/1953 | Archer | 549/27 |
| 3,294,803 | 12/1966 | Rosi et al. | 549/392 X |
| 3,711,513 | 1/1973 | Schulenberg | 549/27 |

OTHER PUBLICATIONS

Archer et al., JACS, vol. 74 (1952), pp. 4296-4308.

*Primary Examiner*—Richard L. Raymond
*Attorney, Agent, or Firm*—McGlew and Tuttle

[57] ABSTRACT

7-Hydroxylucanthone and 7-hydroxyhycanthone derivatives have been found to have significant antitumor effect. The derivatives are of the general formula:

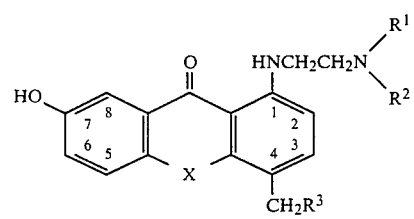

wherein the radicals $R^1$ and $R^2$ are lower alkyl groups or other simple groups and $R^3$ is OH where X=O, and H or OH where X=S.

15 Claims, No Drawings

7-HYDROXYLUCANTHONE, 7-HYDROXHYCANTHONE AND THEIR ANALOGS

The invention described herein was made in the course of work under a grant or award from the Department of Health and Human Services.

CROSS-REFERENCE TO RELATED APPLICATIONS

This application is a continuation-in-part of an application by the same inventor for 7-hydroxylucanthone, serial number 405,37 8, filed July 8, 1982, and for 7-hydroxyhycanthone, serial number 396,433, filed Aug. 5, 1982, both abandoned.

FIELD AND BACKGROUND OF THE INVENTION

The present invention relates in general to antitumor compounds and, in particular to novel compounds of 7-hydroxylucanthone, 7-hydroxyhycanthone, and their derivatives.

It is known that lucanthone (I) and its metabolite, hycanthone (II), possess antitumor activity.

where for:
(I) R=CH$_3$ (lucanthone)
(II) R=CH$_2$OH (hycanthone).

In the National Cancer Institute (NCI) Screening System on P-388 leukemic mice, (I) has a T/C=160 and (II) has a T/C=166 at a dose of about 60 mg/kg. In the NCI screen, a T/C=125 is considered active and T/C greater than 175 is considered to be worthy of further study as a drug of possible future clinical interest.

If leukemic mice are first treated with metabolic inhibitor however, lucanthone is inactive in an antitumor test.

Since hycanthone (II) is a metabolic of lucanthone, it was thought that it might be the active antitumor agent of lucanthone (I). However, when the mice were treated with a metabolic inhibitor and then given hycanthone, the antitumor activity of hycanthone was abolished also.

The NCI screening test is conducted by infecting two groups of white mice with P-388 lymphotcytic leukemia cells.

The first group of mice are held as a control (C) and predictably die after ten days. The remaining group is treated with (T) by a certain dosage of substance suspected ot have antitumor characteristics for a period of 10 days or for a shorter period, for example two or five days. The number of days behond the ten days that members of the test group (T) survive is utilized in a ratio which is multiplied by 100 to obtain the T/C ratio.

Various derivatives which are structurally similar to compounds (I) and (II) have been disclosed in U.S. Pat. No. 3,577,558 to Rosi and No. 2,653,949 to Archer.

The Rosi patent discloses a tricyclic structure similar to the compound (II) with the possibility of substituting one of the hydrogens in the left ring, at positions 5, 6, 7, or 8 with halo, a lower alkyl or lower-alkoxy. Nowhere is it disclosed that the hydrogen at the 5, 6, 7, or 8 position should be substituted by a hydroxy radical nor that the hydroxy radical should specifically at the 7 position. As will become apparent hereinunder, this substitution and positioning of the hydroxy radical produces new and unexpected results with regard to the anti-tumor activity.

The previous Archer patent discloses a ring structure similar to compound (I) with a hydrogen at the 6 position (according to the convention adopted here) substituted by a halo, a lower-alkyl or a lower-alkoxy radical. Here, again, there is no suggestion that a hydrogen of the left ring should be substituted by a hydroxy group nor that that group should be positioned at the 7-carbon position.

The treatment of mice with the metabolic inhibitor has been disclosed in an article entitled "Antibiotics" by E. Hirschberg, Volume III, J. W. Corcoran and F. E. Hahn, Eds., Springer Verlag, Berlin and Heidelberg, 1974, p. 276.

The mechanism by which lucanthone and hycanthone act as antitumor agents has been shown to be through intercalation into the DNA molecule. See E. F. Gale et al, "The Molecular Basis of Antibiotic Action", Wiley, N.Y., 1972 pp. 188 et seq. According to this mechanism the lucanthone or hycanthone molecules position themselves between the base pairs of the DNA molecule. If in addition chemical bonds are formed between the lucanthone or hycanthone molecules and the DNA, the intercalation becomes more permanent and the DNA replication mechanism is rendered inoperative.

SUMMARY OF THE INVENTION

It has been found that, according to the invention, ring-hydroxylated derivatives of lucanthone, more specifically 7-hydroxylucanthone derivatives, are far more active than lucanthone as antitumor agents as shown in Table I.

TABLE I

| COMPOUND | T/C vs P-388 |
| --- | --- |
| (I) (as shown) | 160 |
| (III) | 188 |
| (IV) | 265 |

The hycanthone analogs of (III) and (IV) has been prepared and tested as well.

The lucanthone compounds can be prepared according to a method here labelled A and set forth below. The hycanthone compounds are prepared according to a method B which is also set forth below. NCI screening test results have been conducted for various derivatives of lucanthone and hycanthone, at various dosage levels and the results of these tests are set forth below in Table II. Table II includes comparative cases as well, to show how a position change of the hydroxy radical (e.g. from 7-carbon to 6-carbon) and substitution of a loweralkoxy for the hydroxy, effect antitumor activity. Cases where the sulfur atom has been replaced by oxygen (X=O) have also been prepared and tested with results shown in Table II.

rolidinyl, piperidyl, morpholinyl, piperazinyl and N-substituted piperazinyl; and $R^3$ is H or hydroxy.

Where X=O: $R^1$ and $R^2$ are individually selected from one of, lower alkyls, and jointly selected from one of, pyrrolidinyl, piperidyl, morpholinyl, piperazinyl and N-substituted piperazinyl; and $R^3$ is hydroxy.

DESCRIPTION OF THE PREFERRED EMBODIMENTS

TABLE II

[Structure shown: dibenzo compound with HO at position 7, carbonyl bridge, X at bridging position, CH3R3 substituent at 4, and HNCH2CH2N(R1)(R2) at position 1]

| Compound # or Ring Substituent | $R^1$ | $R^2$ | $R^3$ | X | Method of Preparation | Dose (mg/kg) | T/C | Days Treated |
|---|---|---|---|---|---|---|---|---|
| II | C2H5 | C2H5 | H | S | A | 100 | 123 | 9 |
|  | C2H5 | C2H5 | H | S | A | 50 | 188 | 9 |
|  | C2H5 | C2H5 | H | S | A | 25 | 159 | 9 |
|  | C2H5 | C2H5 | H | S | A | 12.5 | 142 | 9 |
| I | CH3 | CH3 | H | S | A | 128 | Toxic | 9 |
|  | CH3 | CH3 | H | S | A | 64 | 265 | 9 |
|  | CH3 | CH3 | H | S | A | 32 | 191 | 9 |
|  | CH3 | CH3 | H | S | A | 16 | 170 | 9 |
|  | CH3 | CH3 | H | S | A | 8 | 180 | 9 |
|  | CH3 | CH3 | H | S | A | 4 | 141 | 9 |
|  | CH3 | CH3 | H | S | A | 2 | 139 | 9 |
|  | CH3 | CH3 | H | S | A | 1 | 130 | 9 |
| V | C2H5 | C2H5 | OH | S | B | 75 | 207 | 2 |
|  | C2H5 | C2H5 | OH | S | B | 37.5 | 179 | 2 |
|  | C2H5 | C2H5 | OH | S | B | 18.75 | 207 | 2 |
|  | C2H5 | C2H5 | OH | S | B | 9.88 | 162 | 2 |
| VI | CH3 | CH3 | OH | S | B | 200 | 222 | 5 |
|  | CH3 | CH3 | OH | S | B | 100 | 194 | 5 |
|  | CH3 | CH3 | OH | S | B | 50 | 175 | 5 |
|  | CH3 | CH3 | OH | S | B | 25 | 160 | 5 |
| (6-OH) | CH3 | CH3 | H | S | A | 200 | 126 | 9 |
| (7-OCH3) | C2H5 | C2H5 | H | S | A | 100 | 147 | 9 |
| (7-OCH3) | CH3 | CH3 | H | S | A | 100 | 135 | 9 |
| (7-OH) | CH3 | CH3 | OH | O | — | 100 | 198 | 9 |
| (7-OH) | C2H5 | C2H5 | OH | O | — | 100 | 214 | 9 |
| (7-OH) | —N(CH2—CH2)(CH2—CH2) |  | OH | O | — | — | — | — |

According to these results, and results obtained for numerous other lucanthone derivatives which have shown less antitumor activity, it is believed that a compound, according to the invention which has useful antitumor characteristics has the general structure:

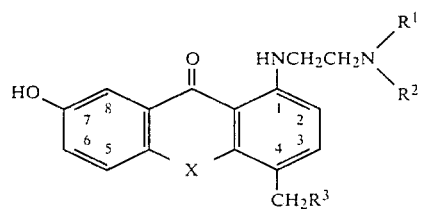

wherein, for X=S:

$R^1$ and $R^2$ are individually selected from one of, lower alkyls, and jointly selected to form one of, pyr-

EMBODIMENTS

The compounds of this invention which have been found to have significant antitumor effect can be synthesized in various ways. Method of preparation A is as follows:

The preparation of the 7-hydroxylucanthone analogues was carried out as shown in Scheme I (See S. Archer and C. M. Suter, J. Am. Chem. Soc., 74, 4296 (1952).

Scheme 1

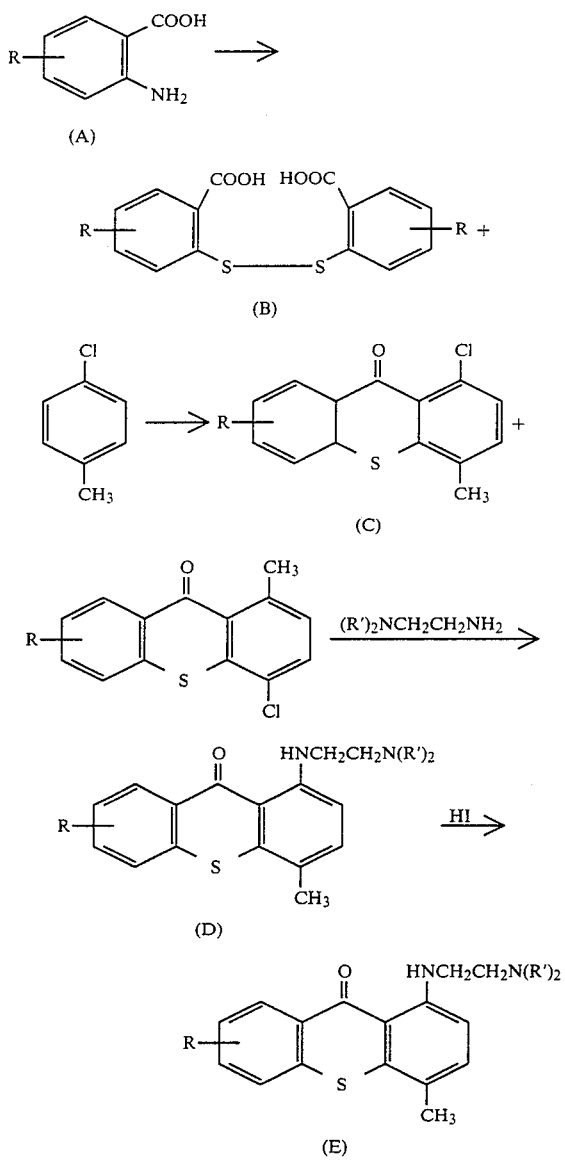

5-Methoxyanthranilic acid was diazotized and converted to the corresponding dithiosalicylic acid, and the unpurified acid were condensed with p-chlorotoluene and to give the mixed thioxanthenones. The isomers which contained the more reactive 1-chloro substituent, were allowed to react with N,N-diethylethylenediamine and N,N-dimethylethylenediamine, as described by Archer et al to give the corresponding 1-[[2-(Dialkylamino)ethyl]amino]-7-methoxy-4-methyl-9H-thioxanthen-9-one. These gave the (7-OCH3) substituted compounds of Table II. Demethylation of the methoxythioxanthenones with 48% HI proceeded smoothly in each case to give the target compounds I and II, which were purified as the hydriodide salts.

With R=5-OCH3 in compound (A) alone and R=5-OCH3 in (B), the process, in greater detail is as follows:

METHOD A

5-Methoxydithiosalicylic Acid (B).

Ten grams of 5-methoxyanthranilic acid (A) was converted to the corresponding dithio acid. A solution of (A) in concentrated HCl and H2O was cooled to 5° C. and diazotized with a solution of NaNO2 in H2O. The diazonium solution was filtered and added slowly to a cold solution of Na2S2 prepared from Na2S.9H2O dissolved in H2O to which was added S and NaOH in H2O. The mixture was left overnight, filtered, and cautiously acidified with concentration HCl. There was obtained 8.5 g (78%) of the desired dithio acid, mp 302°–305° C. after two crystallizations from 2-methoxyethanol.

1-[[2-(Dimethylamino)ethyl]amino]-7-methoxy-4-methyl-9H-thioxanthen-9-one (D, where R=7-OCH3 and R1=CH3) and 1-[[2-(Dimethylamino)ethyl]amino]-7-hydroxy-4-methyl-9H-thioxanthen-9-one (E, where R=7-OH and R1=CH3). A mixture of 12.3 g of 5-methoxydithiosalicyclic acid (B), 34 mL of p-chlorotuolene, and 130 mL of concentrated H2SO4 was heated with stirring on the water bath. This furnished 9.0 g of a mixture of isomeric 7-methoxythioxanthenones. A suspension of 3.2 g of this mixture in 8 mL of N,N-dimethylethylenediamine was refluxed overnight. The excess diamine was removed by distillation with steam. The residue was dissolved in glacial acetic acid, diluted with H2O, and filtered to remove the unreacted 4-chloro-7-methoxy-1-methylthioxanthenone. Basification of the filtrate furnished the desired product (D): mp 141°–143° C. after crystallization from EtOH; yield 1.55 g.

A suspension of 1.55 g of (D) in 12 ml of 48% HI, was refluxed for 3 hours, cooled and filtered. Recrystallization from MeOH gave 1.7 g of the HI salt of E, M.P. 273°–275° C.

1-[[2-(Diethylamino)ethyl]amino]-7-hydroxy-4-methyl-9H-thioxanthen-9-one (A)

2-((Diethylamino)ethyl)amino)-7-methoxy-4-methyl-9H-thioxanthen-9-one

Using the same procedure as described above, but substituting an equivalent amount of N,N-diethylethylenediamine for N,N-dimethylethylenediamine, there was obtained the desired ((2-(diethylamino)ethyl)amino)-7-methoxy-4-methyl-9H-thioxanthen-9-one as the free base, mp 81°–82° C. after crystallization from ethanol.

(B)

1-[[2-(Diethylamino)ethyl]amino]-7-hydroxy-4-methyl-9H-thioxanthen-9-one

Treatment of the above compound with 48% hydriodic acid followed by reflux for 3 h gave, upon cooling the hydriodide of the desired compound, mp 254°–255° C. after crystallization from methanol.

1-(2-Dimethylaminoethylamino)-7-hydroxy-4-(hydroxymethyl)-9H-thioxanthen-9-one

5-Methoxythiosalicylic Acid. A suspension of 1.0 g of 5-methoxy-dithiosalicylic acid (A) and 500 mg of Zn dust in 10.0 mL of acetic acid was vigorously stirred under reflux for 4 h. During this time an additional 500 mg of Zn dust and 5.0 mL of acetic acid were added. The mixture was cooled and filtered. The solid was washed with water, air-dried, and suspended in 40 mL of boiling H2O. A solution of 4.0 g of NaOH in 10 mL of H2O was added carefully while the suspension was kept under reflux. The warm suspension was filtered, and the filtrate was acidified to precipitate the desired acid: yield 600 mg (60%); mp 170°–175° C. After two crystallizations from C₂H₅OH-H₂O, a sample was melted at 173°–178° C. When run on an 11.0-g scale, there was obtained, after one crystallization from EtOH-H₂O, 7.0 g of the acid (64%), mp 174°–178° C.

The method of preparation B for preparing the hycanthone analog (VI) is as follows:

3-Chloro-2′-carboxy-4′-methoxydiphenylsulfide (1)

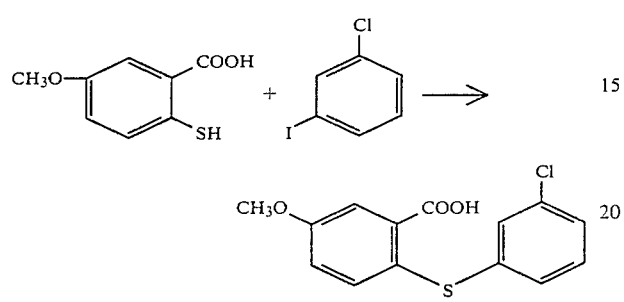

A mixture of 9,2 g of 5-methoxythiosalicylic acid and 14.0 g of dry K₂CO₃ was stirred and heated at 120° for 10 min in 120 mL of DMF. There was added 12.0 g of m-chloroiodobenzene, 400 mg of Cu bronze and 200 mg of CuI and stirring and refluxing were continued for 30 hours. The cooled suspension was filtered and the filtrate was evaporated to ⅓ volume in vacuo. The residue was diluted with H₂O and acidified with HCl. The oily product which separated rapidly solidified while stirring. The solid was filtered, washed with H₂O and dried to obtain Wt. 11.5 g (78%) of material suitable for the next step. After crystallization from 70% EtOH the compound melted at 152°–153°.

1-Chloro-7-methoxythioxanthenone (2)

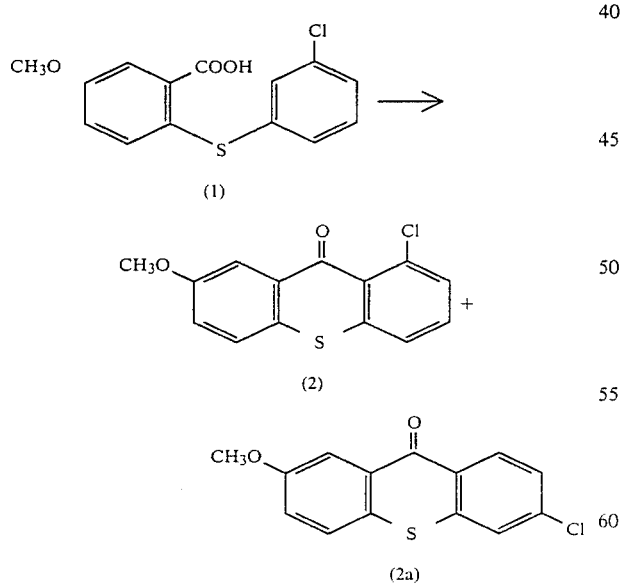

Ten grams of diphenylsulfide (1) was added to 40.0 g of polyphosphoric acid (PPA) at 130° C. The solution was stirred at this temperature for 4 hours, allowed to cool, and then poured into cold H₂O. The solid that separated was filtered, washed with H₂O, dilute NH₄OH solution and again with H₂O. After drying overnight, the mixture of (2) and (2a) weighed 8.2 g (88%). The mixture melted at 155°–171° C. after crystallization from ethanol.

1-[[2-(Dimethylamino)ethyl]amino]-7-methoxy-9H-thioxanthen-9-one

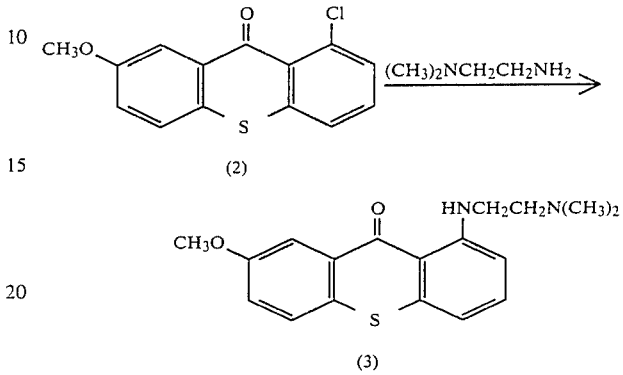

A suspension of 7.0 g of the mixed thioxanthenones (2) and (2a), 4.0 mL of dimethylaminoethylamine and 12 mL of pyridine was heated under reflux in an oil bath (170° C.) for 20 hours. The cooled reaction mixture was made strongly basic with 10% KOH solution and steam-distilled to remove most of the volatile organic bases. After cooling, the dark-yellow solid was collected on a filter. It was treated with 10% HCl to dissolve the product, filtered to remove unreacted (2a) and the filtrate was made strongly basic with 10% KOH solution. The product which separated was filtered, washed with H₂O and dried to give 4.6 g (55%) of (3). After crystallization from ethanol, the base melted at 113°–114° C.

Anal. Calcd for C₁₈H₂₀N₂O₂S (328.3); C, 65.82; H, 6.14; N, 8.53. Found C, 65.85; H, 6.13; N, 8.56.

It is noted that the yield was based on the mixture (2) and (2a). The ratio of isomers in this mixture is unknown.

1-(2-Dimethylaminoethylamino)-7-hydroxythioxanthenone (4)

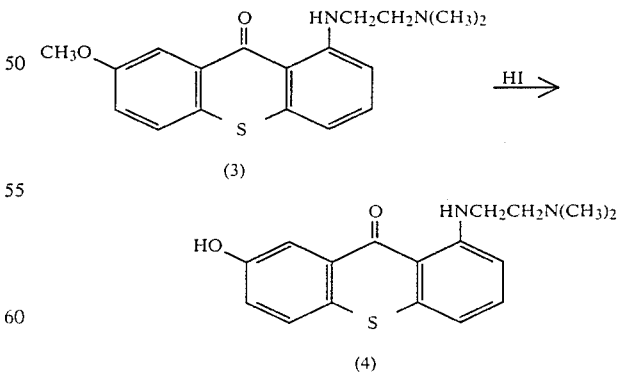

A suspension of 4.0 g of (3) in 40 mL of HI (56%) was refluxed for 3 hours during which time an orange compound separated. The cooled mixture was filtered and the collected solid was sucked as dry as possible and washed with ether. The HI salt was dissolved in H₂O and made strongly basic with 20% NaOH to dissolve the product. The cloudy solution was filtered (Celite) and the filtrate was neutralized with HOAc whereupon crystals separated. They were collected, washed with H₂O and dried. Wt. 2.47 g (65%). The base (4) was crystallized from EtOH. M.P. 174°–176° C.

Anal. Calcd for C₁₇H₁₈N₂O₂S(314.3): C, 64.94; H, 5.77; N, 8.91. Found: C, 64.63; H, 5.77; N, 8.78.

1-[[2-Dimethylamino)ethyl]amino]-7-toluenesulfonyloxy-9H-thioxanthen-9-one (5)

in formula 4, place a line connecting the right-hand ring to the N atom of the chain "HNCH₂CH₂N(CH₃)₂".

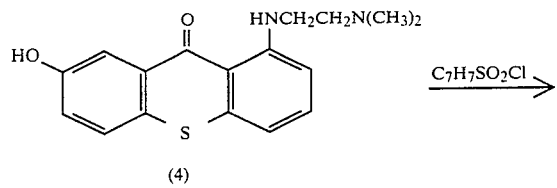

(4)

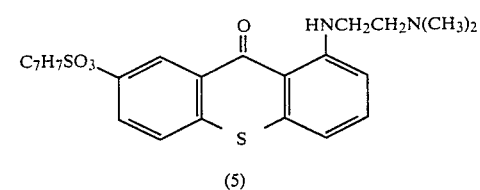

(5)

A solution of 2.3 g of (4) in 20 ml of dry pyridine was stirred while 1.5 g of p-toluenesulfonyl chloride was added portionwise. After all was washed the mixture was stirred for 30 minutes and poured into cold water. The mixture was made strongly basic with 20% Na₂CO₃ and the suspension was allowed to settle. The supernatant was decanted carefully and the semi-solid residue was triturated with H₂O, a procedure which induced it to crystallize. It was filtered, washed thoroughly with water and dried to leave 2.9 g (84%) of material suitable for use in the next step. After recrystallization from EtOH, the tosylate (5) melted at 118°–119° C.

Anal. Calcd for C₂₄H₂₄N₂O₄S₂(468.6): C, 61.65; H, 5.16; N, 5.98. Found: C, 61.46; H, 5.13; N, 5.94.

1-[[2-Dimethylamino)ethyl]amino]-4-(hydroxymethyl)-7-(toluenesulfonyloxy)-9H-thioxanthen-9-one (6)

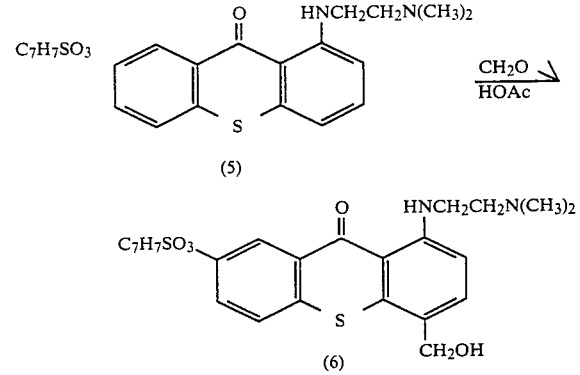

A solution of 2.5 g of (5) in 400 ml of 37% formaldehyde, containing 10 mL of 5N HOAc was stirred and heated at 70° C. (internal temperature) for two days. The cooled solution was made basic with 10% Na₂CO₃ solution and the remaining suspension was extracted with 3×150 mL portions of CHCl₃. The solvent was removed and the residue was chromatographed on 40 g of silica gel using CHCl₃-CH₃OH as the eluant. Starting material was eluted with CHCl₃-1–3% CH₃OH mixtures. The desired material (6) was eluted with CHCl₃-4% MeOH and CHCl₃-6% MeOH. These eluates were combined and evaporated to give 1.7 g of (6) (64%) which melted at 175°–176° C. after crystallization from CH₃OH.

Anal. Calcd. for C₂₅H₂₆N₂O₅S₂(498.6): C, 60.22; H, 5.26; N, 5.62. Found: C, 60.32; H, 525; N, 5.60.

1-[(2-Dimethylamino)ethyl]amino]-7-hydroxy-4-(hydroxymethyl)-9H-thioxanthen-9-one (7)

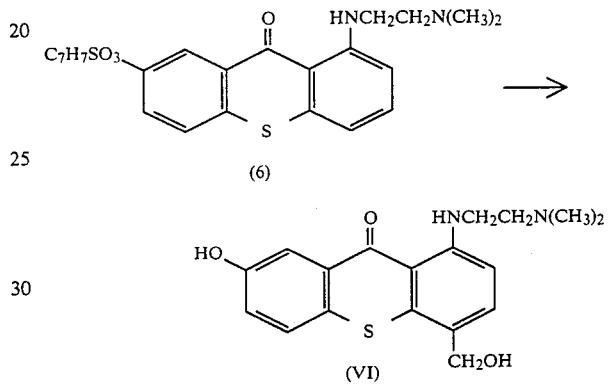

(6)

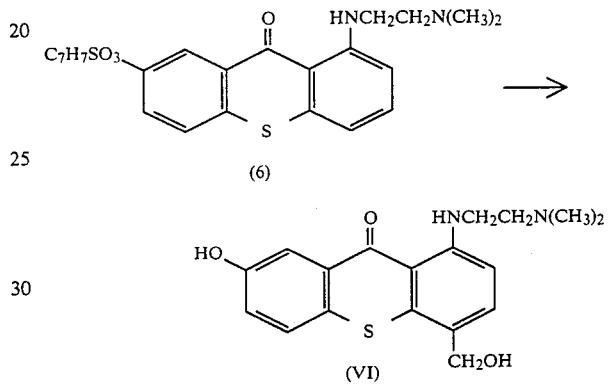

(VI)

A solution of 1.4 g of (6) in 20 ml of ethanol containing 4 mL of 5N KOH was refluxed for 30 minutes. The ethanol was evaporated and the residue was dissolved in 50 mL of H₂O. The filtered solution was neutralized with HOAc and then made slightly alkaline with a solution of KHCO₃. The yellow crystalline solid, wt 0.960 g (100%) was filtered and recrystallized from methanol. It darkened at about 176° C. and melted with decomposition at about 250° C.

Anal. Calcd for C₁₈H₂₀N₂O₃S(344.2); C, 62.76; H, 5.85; N, 8.14. Found: C, 62.42; H, 5.90; N, 8.09.

A superior process of making an important intermediate in the hycanthone series can be synthesized according to the following equation (identified as the CF₃SO₃H equation):

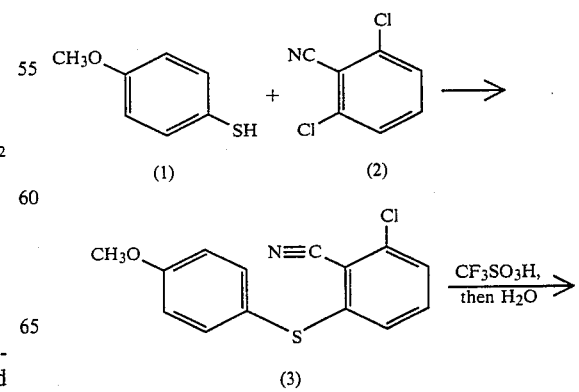

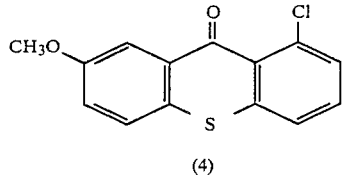

(4)

the chemical name for CF₃SO₃H being trifluoromethane-sulfonic acid.

The advantages of this method are:

(a) p-methoxythiophenol (1) and 2,6-dichlorobenzonitrile (2) are commercially availalbe.

(b) The 1-chloro-7-methoxythioxanthenone (4) is obtained as a pure entity uncontaminated by the isomeric 3-chloro-7-methoxy-thioxanthenone.

(c) The entire sequence to prepare (4) is far shorter than the older method.

(d) Because of the fact that the method is shorter and pure (4) is obtained, the overall conversion is far higher.

The details of the preparation are given below.

1-Chloro-7-methoxythioxanthenone

It is noted that 1-chlorothioxanthenone had been prepared (see the Rosi patent) by condensing p-methoxybenzenethiol with 2,6-dichlorobenzonitrile followed by ring closure in hot polyphosphoric acid (PPA). In the present invention, the PPA method does not work. It was found that trifluoromethane-sulfonic acid at temperatures in the range of 25°–80° gave the desired product as shown in the above equations.

Details of that equation follow:

20 g of potassium t-butoxide was added to a solution of 25 g of p-methoxybenzenethiol in 350 mL of dry dimethyl sulfoxide. After stirring for 10 minutes, 29 g of 2,6-dichlorobenzonitrile was added and the mixture was stirred at room temperature for two hours and then on the steam-bath for three hours. The mixture was poured into 3 L of ice water, a solution of sodium hydroxide was added and the solid that separated was collected on a filter and dried. The crude material was boiled in ethanol and filtered. The filtrate was evaporated to a small volume and cooled to give 35 g (75%) of 2-chloro-6-(p-methoxybenzenethio)benzonitrile. (3) M.P. 109°–110° C. after crystallization from ethanol.

Anal. Calcled for $C_{14}H_{10}ClNOS(275.8)$: C, 60.97; H, 3.66; N, 5.08. Found: C, 61.09; H, 3.77; 5.06.

1-Chloro-7-methoxythioxanthenone (4) 2 g of the above nitrile was added to 8 mL of trifluoromethanesulfonic acid over a period of 20 minutes. The mixture was stirred at room temperature for 4 hours and then poured on ice. The suspension was extracted with chloroform and the chloroform extracts were taken to dryness. The residue was purified by column chromatography to give the desired thioxanthenone. M.P. 175°–184° C. On treatment with N,N-dimethylethylenediamine, it gave the desired 1-(2-dimethylaminoethylamino)-7-methoxythioxanthenone (identical with the material prepared as described above).

The 6-hydroxy analogues, (6-OH) in Table II, was prepared by the sequence shown in Scheme II.

Scheme II

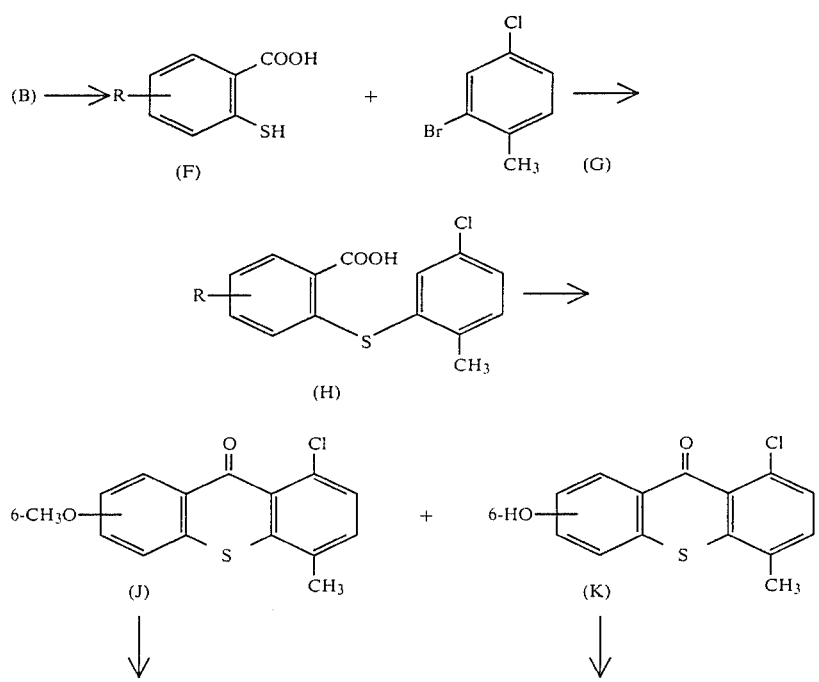

Scheme II
-continued

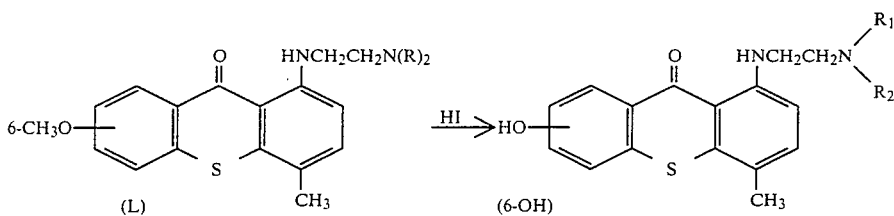

4-Methoxyanthranil acid was (see J. M. L. Stephens et al, *J. Chem. Soc.* 1034, 1947) used as the starting material to prepare 4-methoxythiosalicylic acid (F), which was converted to 2-[(5-chloro-2-methylphenyl)thiol-4-methoxybenzoic acid (H). Cyclization in $H_2SO_4$ gave (J) which, with the requisite N,N-dialkylethylenediamines, gave (L) which was smoothly demethylated to give (6-OH).

1-[[2-Dimethylamino)ethyl]amino]-4-(hydroxymethyl)-7-methoxy-9H-thioxanthen-9-one. A solution of 100 mg (0.30 mmol) of 1-[[2-dimethylaminoethyl-]amino]-7-methoxy-9H-thioxanthene-9-one in 5 mL of 37% formalin and 0.1 mL of 5N acetic acid was heated on a steam bath for 4 hr as in the case of the diethylamino analogue. Chromatography on silica gel with $CHCl_3$-$CH_3OH$ as the eluting solvent gave 7.0 mg of starting material and 37 mg (35%) of the desired product, which melted at 153°–156° C. after crystallization from $C_2H_5OH$.

1-[[2-Dimethylamino)ethyl]amino]-7-methoxy-9-oxo-9H-thioxanthene-4-carboxaldehyde. The above hydroxymethyl derivative (1.20 g) was stirred with 2.6 of activated $MnO_2$ in 200 mL of dry ether under reflux for 2 h. The cooled suspension was filtered and the filtrate was evaporated to dryness and the residue was chromatographed. The desired aldehyde was eluted from the silica gel column with $CHCl_3$-2%$CH_3OH$: yield 600 mg (50%). The analytical sample, mp 170°–172° C. was prepared by recrystallization from $C_2H_5OH$.

1-[[2-(Dimethylamino)ethyl]amino]-7-hydroxy-9-oxo-9H-thioxanthene-4-carboxaldehyde. A mixture of 4.13 g (12 mmol) of the methoxyaldehyde 4 and 55 g pyridine hydrochloride was heated at 185° C. for 1.5 h in a vessel protected from moisture: The cooled mixture was diluted with $H_2O$, and the crystals were collected by filtration. These were dissolved in $H_2O$, and the solution was made alkaline with $K_2CO_3$. The crop of crystals that separated was set aside. The filtrate from the original filtration was made alkaline with $K_2CO_3$ and extracted from $CHCl_3$. Evaporation of the $CHCl_3$ extract left a crystalline residue, which combined with the first crop of crystals: yield 3.4 g (83%); mp 219°–220° C.

1-[[2-(Dimethylamino)ethyl]amino]-7-hydroxy-4-(hydroxymethyl)-9H-thioxanthen-9-one. A solution of 650 mg (1.9 mmol) of the above aldehyde in 100 mL of $CH_3OH$ was reduced with 400 mg of $NaBH_4$. The crystals that were obtained were purified by crystallization from $CH_3OH$: yield 500 mg (77%); mp > 350° C. dec.

An alternative procedure for the preparation of this compound starts from 1-[[2-(Dimethylamino)ethyl-]amino]-7-methoxy-9H-thioxanthen-9-one (see above).

1-[[2-(Diethylamino)ethyl]amino]-7-hydroxy-4-(hydroxymethyl)-9H-thioxanthen-9-one. 1[[2-(Diethylamino)ethyl]amino] and 3-[[2-(Diethylamino)ethyl-]amino]-7-methoxy-9H-thioxanthen-9-one. A mixture of 360 mg (1.3 mmol) of the mixed 7-methoxy-9H-thioxanthen-9-ones and 3.0 mL of N,N-diethylethylenediamine was heated under reflux for 18 h while protected from moisture. The suspension was cooled and poured into $H_2O$, and 10 mL of 20% KOH was added. The apparatus was set for downward distillation, and 20 ml of distillate was collected. The cooled suspension was made acidic with acetic acid, diluted to 75 mL, and filtered. The filtrate was made basic, and the oil that separated was extracted with $CHCl_3$. The dried extracts were evaporated to dryness to leave an oil, which was chromatographed on a column of 20 g of silica gel. The desired product was eluted with $CHCl_3$; yield 120 mg; mp 71°–73° C., after which crystallization from $C_2H_5OH$ melted at 71°–72° C.

The next fraction was eluted with $CHCl_3$-$CH_3OH$ (19:1). The NMR-indicated that it was the 3-isomer. It formed a fumarate, mp 172°–174° C., after crystallization from absolute EtOH.

1-[[2-(Diethylamino)ethyl]amino]-4-(hydroxymethyl)-7-methoxy-9H-thioxanthen-9-one A solution of 2.70 g (7.5 mmol) of 1-[[2-(Diethylamino)ethyl]amino]-7-methoxy-9H-thioxanthen-9-one in 135 ml of 37% formalin containing 2.7 ml of N acetic acid was heated on the steam bath for 4 hr, cooled and made alkaline with 10N NaOH solution. The suspension was taken up in $CHCl_3$. The extract was evaporated to dryness and covered with $CHCl_3$. The extract was evaporated to dryness and covered with $C_2H_5OH$. The "dimer" separated: yield 400 mg. It was recrystallized from 2-methoxy-ethanol. The filtrate was evaporated to dryness to leave an oil, which, after chromatography on silica gel with $CHCl_3$-$CH_3OH$ as the eluant, furnished 1.30 g (44.5%) of the desired product, mp 103°–105° C. after crystallization from ethyl acetate-petroleum ether.

1[[2-Diethylamino)ethyl]amino]-7-methoxy-9-oxo-9H-thioxanthene-4-carboxaldehyde

A solution of 1.25 g (0.32 mmol) of the (hydroxymethyl)thioxanthenone in 300 mL of dry ether was treated with 2.60 g of activated $MnO_2$ and stirred under reflux for 2 h in a vessel protected from moisture. The suspension was stirred overnight at room temperature and filtered. The filtrate was evaporated to dryness, and the residue was chromatographed on 40 g of silica gel with $CHCl_3$-$CH_3OH$ as the eluting solvent. The aldehyde was eluted in the $CHCl_3$-3% $CH_3OH$ fraction: yield 0.8 g (64%); mp 125°–127° C.

1-[[2-(Diethylamino)ethyl]amino]-7-hydroxy-9-oxo-9H-thioxanthene-4-carboxaldehyde A mixture of 600 mg (1.56 mmol) of the methoxyaldehyde and 6.0 g of pyridine hydrochloride was heated at 140° C. for 3.5 h in a vessel protected from moisture. The mixture was cooled and treated with $H_2O$. The clear aqueous solution was made alkaline by the cautious addition of solid $K_2CO_3$. The suspension was extracted with $CHCl_3$, and the solvent was removed by evaporation. The residue was chromatographed on a column of silica gel (30 g). The eluant solvent was $CHCl_3$-$CH_3OH$. There was recovered the starting material in the $CHCl_3$/1–2% $CH_3OH$. The $CHCl_3$/4–7% $CH_3OH$ fractions furnished 100 mg of a crude product, which, after crystallization from 95% $C_2H_5OH$, furnished 77 mg (13% as the hydrate) of the hydroxyaldehyde, mp 85°–90° C.

Anal. Calcd for $C_{20}H_{22}N_2O_3S \cdot H_2O$: C, 61.83; H, 6.23; N, 7.21. Found: C, 62.31; H, 5.77; N, 7.09.

1-[[2-(Diethylamino)ethyl]amino]-7-hydroxy-4-(hydroxymethyl)-9H-thioxanthen-9-one(5)

To a solution of 85 mg (0.23 mmol) of the aldehyde 25 in 20 mL of $CH_3OH$ was added 40 mg of $NaBH_4$ in one portion. After the solution was stirred at room temperature for 1.0 h, the solvent was evaporated in vacuo, and $H_2O$ was added to the residue. The suspension was adjusted to pH 8 by careful addition of dilute acetic acid, and the crystals that separated were collected and recrystallized from $CH_3OH$: yield 46 mg (54%); mp 182°–184° C.

An alternate procedure starting from 1-[[2-(Diethylamino)ethyl]amino]-7-methoxy-9H-thioxanthene-9-one is as follows:

1[[(2-Diethylamino)ethyl]amino]-7-hydroxy-9H-thioxanthen-9-one

A solution of 1.50 g (4.2 mmol) of the methoxy compound in 15 mL of 56% HI solution was refluxed for 3 h and cooled. The crystals that separated were collected, washed with ether, and dried. They were dissolved in 10% NaOH, the solution was filtered, and the filtrate was neutralized with dilute acetic acid. The suspension was extracted with $CHCl_3$, and the dried extract was evaporated to leave 1.22 g (83%) of the phenol, which melted at 157°–158° C. after crstyallization from 70% aqueous methanol.

1-[[2-(Diethylamino)ethyl]amino]-7-(toluenesulfonyloxy)-9H-thioxanthen-9-one To a stirred solution of 1.40 g (4.1 mmol) of the above 9H-thioxanthen-9-one and 15.0 ml of dry pyridine there was added 0.95 g (5.0 mmol) of toluenesulfonyl chloride. The reaction mixture was stirred at room temperature in a flask protected from moisture for 1 h. The contents were then poured into cold water, and the suspension was extracted with ether. The extract was washed with water, dried, and evaporated to dryness to leave an oil: yield 2.0 g (99%). It was characterized as a crystalline fumarate, mp 127°–128° C. after crystallization from $CH_3OH$.

1-[[2-Diethylamino)ethyl]amino]-4-(hydroxymethyl-7-(toluenesulfonyloxy)-9H-thioxanthen-9-one A solution of 1.48 g (2.98 mmol) of the oily (toluenesulfonyloxy)-9H-thioxanthene-one, 3 ml of 5N acetic acid, and 150 mL of 37% formalin was stirred while being heated at 60°–70° C. for 48 h. The cooled mixture was made alkaline with $Na_2CO_3$ solution and extracted with the $CHCl_3$. The dried extract was evaporated to dryness, and the residue was chromatographed on silica gel with $CHCl_3$/$CH_3OH$ as the eluant. Some starting material was recovered from the early fractions. Later fractions yielded the desired hydroxymethyl derivative: yield 0.58 g (37%); mp 129°–130° C. after crystallization from $CH_3OH$.

1-[[2-(Diethylamino)ethyl]amino]-7-hydroxy-4-(hydroxymethyl)-9H-thioxanthen-9-one A solution of 0.51 g (0.096 mmol) of the above ester in 15 mL of $C_2H_5OH$ containing 1.5 mL of 5N KOH was refluxed for 1 h. The solvent was evaporated, and the residue was dissolved in 50 mL of $H_2O$ and filtered (Celite). The clear filtrate was neutralized, and the precipitate was collected and crystallized from $CH_3OH$: yield 0.26 g (72%); mp 181°–182° C.

1-[[2-Diethylamino)ethyl]amino]-7-hydroxy-4-(hydroxymethyl)-9H-xanthene-9-one 2-(3-Chlorophenoxy)-5-methoxybenzoic Acid. A suspension of 18.0 g (0.11 mol) of 5-methoxysalicylic acid (27) and 28 g of dry $K_2CO_3$ in 200 mL of dry DMF was heated at 120° C. for 10 min. Then, 25 g (0.1 mol) of m-chloroiodobenzene, 0.5 g of Cu powder, and 0.3 g of CuI were added. The mixture was heated and stirred under reflux for 50 h. The cooled suspension was filtered, and the filtrate was concentrated in vacuo to a small volume. The residue was treated with $H_2O$ and then acidified with HCl. The oil that separated soon solidified. The solid was filtered and the residue was washed with warm $H_2O$ and dried: yield 18 g (61%). After recrystallization from 70% aqueous $CH_3OH$, the crystals melted at 142°–143° C.

1-Chloro-(31) and 3-Chloro-7-methoxy-9H-xanthen-9-one Eighteen grams (0.065 mol) of the above acid was added in one portion to 50 mL of 50% polyphosphoric acid preheated to 120° C. The mixture was stirred at this temperature for 3 h. It was cooled, poured into ice-water, and filtered. The filter cake was washed with $H_2O$, 10% NaOH solution, and again with $H_2O$. The dried mixture weighed 14 g (83%). After crystallization from $CH_3OH$ it melted at 139°–140° C.

1-[[2-(Diethylamino)ethyl]amino]-7-methoxy-9H-xanthen-9-one

A mixture of 10.0 g (38.3 mmol) of the above chloro-9H-xanthen-9-one mixture, 6.0 mL of N,N-diethylethylenediamine, and 20 mL of dry pyridine was heated under reflux for 16 h. The reaction mixture was worked up in the usual way to give 6.5 g of the desired amine, which melted at 135°–136° C. after crystallization from petroleum ether-ether.

1-[[2-(Diethylamino)ethyl]amino]-7-hydroxy-9H-xanthen-9-one

A solution of 8.0 g (23.5 mmol) of the methoxy-9H-xanthen-9-one in 60 mL of 56 HI was heated under reflux for 4 h. The mixture was cooled, and the HI salt of 34 was collected on a filter and washed with ether. It was dissolved in 400 mL of $H_2O$ and made alkaline with NaOH. The solution was clarified by filtration through a bed of Celite, and then the filtrate was carefully neutralized with dilute acetic acid. The yellow crystals were filtered, washed with $H_2O$, and dried: yield 6.6 g (86%). After crystallization from $CH_3OH$, the yellow needles melted at 178°–179° C.

1-[[2-(Diethylamino)ethyl]amino]-7-(toluenesulfonyloxy-9H-xanthen-9-one

Four grams (20 mmol) of p-toluenesulfonyl chloride was slowly added to a stirred solution of 6.0 g (18.0 mmol) of the hydroxy-9H-xanthen-9-one in 30 mL of dry pyridine. The stirred mixture was kept at 50° C. for 1.5 h and then poured onto ice water. The mixture was made strongly alkaline with $Na_2CO_3$ solution, and the crystals that separated were filtered, washed thoroughly with $H_2O$, and dried: yield 7.5 g (85%). After crystallization from ether-petroleum ether, the ether melted at 74°–75° C.

1-[[2-(Diethylamino)ethyl]amino]-7-toluenesulfonyloxy)-4-(hydroxymethyl)-9H-xanthen-9-one A solution of 6.0 g (12.5 mmol) of the (toluenesulfonyloxy)-9H-xanthen-9-one 36 in 700 mL of 37% formalin and 10 mL of N acetic acid was stirred at 70° C. for 12 h. The cooled mixture was made basic with $Na_2CO_3$ solution, and extracted with $CHCl_3$. The dried extract was evaporated to dryness in vacuo at 30° C. The residue was chromatographed on silica gel. The desired product was eluted with $CHCl_3/2$–4% $CH_3OH$ to give 3.8 g (60%) of the hydroxymethyl compound 38, mp 145°–146° C. after crystallization from absolute $C_2H_5OH$.

1-[[2-(Diethylamino)ethyl]amino]-7-hydroxy-4-(hydroxymethyl)-9H-xanthen-9-one A solution of 1.0 g (2.0 mmol) of the (toluenesulfonyloxy)-9H-xanthen-9-one 38 in 20 mL of $C_2H_5OH$ containing 3 mL of 5N KOH was heated on the steam bath for 30 min. The solvent was evaporated and the residue was dissolved in $H_2O$. The solution was clarified by filtration and then neutralized. The base that separated was left overnight and then filtered, and the filtrate was dried: yield 0.63 g (90%).

1-[[2-(Dimethyl)aminoethylamino]-amino]-7-hydroxy-4-(hydroxymethyl)-9H-xanthene-9-one 1-[[2-Dimethylamino)ethyl]amino]-7-methoxy-9H-xanthene-9-one. A mixture of 18.0 g of the mixed 1-chloro and 3-chloro-7-methoxy-9H-xanthene-9-ones, 12.0 mL of N N-dimethylethylenediamine and 40 ml of dry pyridine was heated under reflux for 16 h. The mixture was made basic and steam-distilled to remove volatile bases. The cooled residue was filtered and the solid was dissolved in acetic acid and diluted with water. The suspension was filtered and the filtrate was made basic to precipitate a solid which was filtered, dried and recrystallized from aqueous methanol. Wt. 10.0 g., mp 122°–123° C.

1-[[2-(Dimethylamino)ethyl]amino]-7-hydroxy-9H-xanthen-9-one

A suspension of 9.0 g (29.0 mmol) of the above ester in 70 mL of 56% HI was furnished 7.5 g (87%) of the phenol. After crystallization from $CH_3OH$, the yellow needles melted at 199°–200° C.

1-[[2-(Dimethylamino)ethyl]amino]-7-toluenesulfonyloxy)-9H-xanthen-9-one

A mixture of 7.5 g (25.0 mmol) of the hydroxy-9H-xanthen-9-one and 5.6 g (29.0 mmol) of p-toluenesulfonyl chloride in 45 ml of dry pyridine furnished 10.5 (92%) of the ester 37, mp 139°–140° C. after crystallization from $CH_3OH$.

1[[2-(Dimethylamino)ethyl]amino]-7-(toluenesulfonyloxy)-4-(hydroxymethyl)-9H-xanthen-9-one A solution of 10.0 g (22.1 mmol) of the above xanthenone in 1200 mL of 37% formalin and 30 mL of 5N acetic acid gave 4.86 g (46%) of the hydroxymethyl analogue, mp 176°–178° C. after crystallization from $CH_3OH$.

1-[[2-(Dimethylamino)ethyl]amino]-7-hydroxy-4-(hydroxymethyl)-9H-xanthen-9-one Two grams (4.0 mmol) of the above 4-hydroxymethyl-9H-xanthen-9-one gave, after treatment with aqueous sodium hydroxide, 1.2 g (88%) of the desired phenolic product, mp 199° C. dec after crystallization from $CH_3OH$.

1((2-Pyrrolidino)ethyl)amino-7-hydroxy-4-(hydroxymethyl)-9H-xanthen-9-one (A)

1-[[2-(Pyrrolidino)ethyl]amino]-7-methoxy-9H-xanthene-9-one

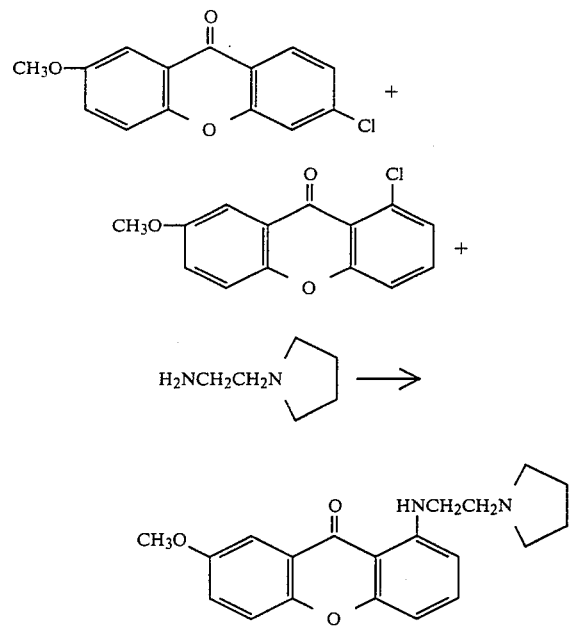

A mixture of 1-chloro and 3-chloro isomers of 7-methoxyxanthone (32.6 g, 0.125 mole) of N-(2-aminoethyl)pyrrolidine (19.43 g, 0.17 mole) were refluxed in 150 mL of pyridine for 24 h with exclusion of moisture. The pyridine and excess of diamine was removed by vacuum distillation (ca. 12 mmHg, bath temp. 60°–72° C.), The distillation residue was dissolved in 200 mL of acetic acid, poured in 1.7 L water filtered and basified with NaOH pellets. The yellow-orange precipitate was filtered, washed with water an dried to give 34 g solid, which was chromatographed on silica gel. The first fraction was eluted with $CHCl_3$. It was a mixture of starting chloroisomers and some minor by-products (18.5 g=56.7% melting range 135°–145° C. The desired compound was eluted with $CHCl_3/EtOH$ (80:20) (13 g=30.7%), mp-93°–94° C. The analytical sample was recrystallized from ethanol, mp=92°–93° C.

Anal. Calcd. for $C_{20}H_{22}O_3N$ (388.41) Found: C, 70.98%, H, 6.56%, N, 8.28%; C, 70.89%, H, 6.50%, N, 8.29%

(B)
1-[[2-(Pyrrolidino)ethyl]amino]-7-hydroxy-9H-xanthene-9-one

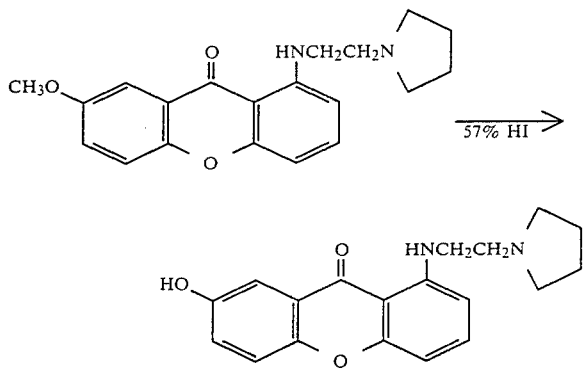

A suspension of th above methoxy-9H-xanthen-9-one (13 g, 38.4 mmol) in 57% HI (80 ml=606 mmol) was refluxed for 3 h. The suspension was cooled, filtered and washed with dry ether. The solid was dissolved in H₂O and neutralized with 20% sodium hydroxide solution. The precipitate was filtered and dried (12.65 g) then boiled in MeOH, filtered hot and washed with MeOH and dried to give 8.6 g phenolic product of mp 192°-194° C.

The methanolic mother liquor was evaporated to dryness and column-chromotographed on silica gel. First, it was eluted with $CHCl_3$/MeOH (80:20) to give 2 g (15.4%) of the starting methoxy compound. Then it was eluted which $CHCl_3$:MeOH (50:50) to give an additional 1.5 g of phenolic product. Total yield on phenolic product: 8.6+1.5=10.1 g (=81.5%). The analytical sample was recrystallized from MeOH, mp-193°-195° C.

Anal. Calcd. for $C_{19}H_{20}O_3N_2$ (324.38) Found: C, 70.35%, H. 6.21%, N, 8.64% C, 70125%, H, 6.19%, N, 8.57%.

(C)
1-[[2-(Pyrrolidino)ethyl]amino]-7-(p-toluenesulfonxy)-9H-xanthen-9-one

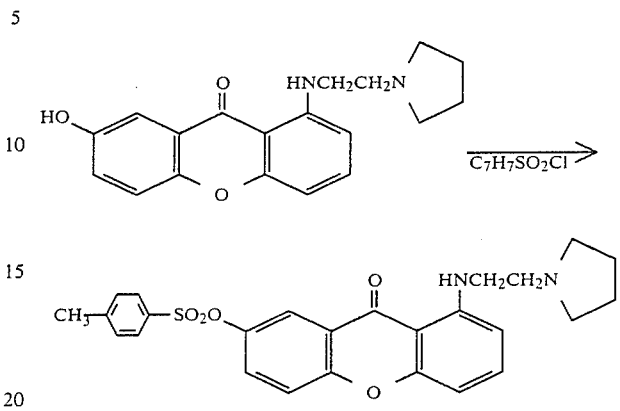

The above 7-hydroxy-xanthone compound (6 g, 0.0018 mole) and p-toluenesulfonylchloride (5.3 g, 0.028 mole) were stirred in 60 mL of pyridine in a bath at 60° C. for 4 h with exclusion of moisture. The dark red solution was then stirred at room temperature overnight (16 h). It was then poured in water (300 mL) and basified with $Na_2CO_3$ solution. The oil did not solidify on standing for 24 h. It was then extracted with ethyl acetate (3×150 mL=450 mL). The combined extracts were evaporated under reduced pressure to gove 7.5 g thick oil, which was column chromatographed on silica gel ($CHCl_3$:MeOH, 95:5) to afford 6.7 g (75.7%) of the TLC-pure sulfonate was an oil. The fumarate salt of the sulfonate crystallized from absolute ethanol after a few days. mp 167°-172° C.

(D)
1[[2-(Pyrrolidino)ethyl]amino]-4-0(hydroxymethyl)-7-(p-toluenesulfonoxy)-9H-xanthene-9-one

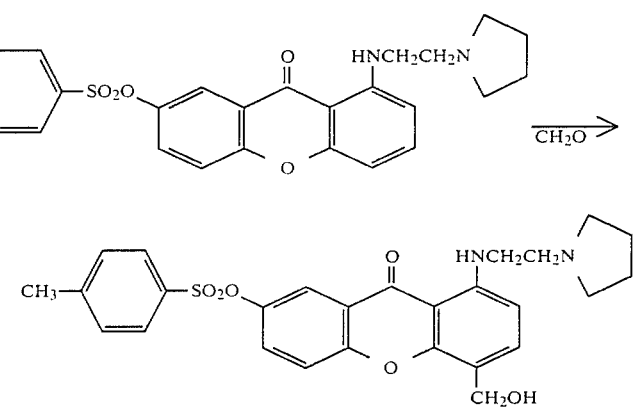

The above xanthone (8.17 g 17,1 mmol) was dissolved in 5N acetic acid (27 ml., 135 mmole) and 37% formaldehyde solution (1.1 L) and stirred in a bath of 67°-72° C. for 72 h. It was then cooled to room temperature, basified with $Na_2CO_3$ solution and extracted with $CHCl_3$. The combined $CHCl_3$ extracts were washed with water, and the solvent removed under reduced pressure to give 10.2 g thick oil, which was column-chromatographed on silica gel. First, there was eluted with $CHCl_3$:MeOH (98:2), 3.30 g (32.4%) of pure starting sulfonate. Elution with CHCl$_3$:MeOH (4–5%) gave the desired product 4.3 g (49.6%). The hydroxymethyl compound was recrystallized from methanol, mp=171°–173° C.

(E)
1[[2-(Pyrrolidino)ethyl]amino]-4-(hydroxymethyl)-7-hydroxy-9H-xanthen-9-one

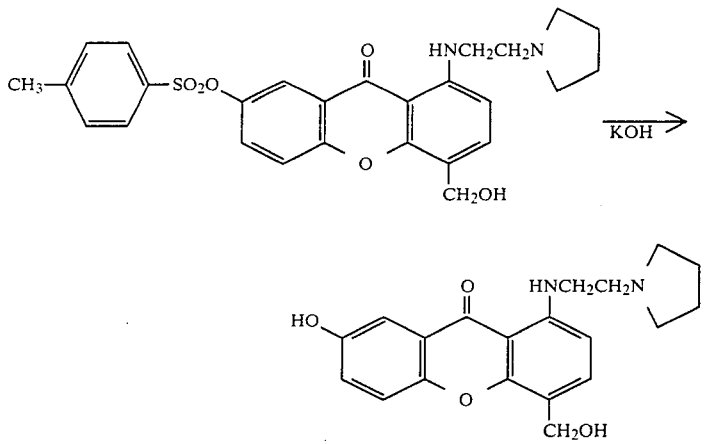

The above 7-(p-toluenesulfonyloxo)xanthone (200 mg, 0.39 mmole) in 15 mL absolute Ethanol and 0.6 mL 5N KOH (3.0 mmole) were refluxed in water bath for 30 min. The condenser was removed to evaporate the ethanol and the residue was dissolved in 10 mL water filtered through a Clite bed and washed with 5 mL water. The alkaline filtrate was neutralized with acetic acid and then made slightly basic with KHCO$_3$ solution. After standing over night, the precipitate was filtered, washed with water thoroughly and dried to give 130 mg (92.9%) yellow solid. The 7-hydroxy-product was recrystallized from MeOH, mp=186°–190° C.

While specific embodiments of the invention have been shown and described in detail to illustrate the application of the principles of the invention, it will be understood that the invention may be embodied otherwise without departing from such principles.

What is claimed is:

1. A compound having the formula

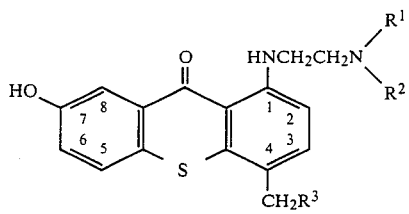

wherein:
R$^1$ and R$^2$ are individually selected from one of, methyl and ethyl;
R$^3$ is selected from one of a hydrogen atom and hydroxy.

2. A compound according to claim 1, wherein R$^1$ and R$^2$ are methyl.

3. A compound according to claim 2, wherein R$^3$ is a hydrogen atom.

4. A compound according to claim 2, wherein R$^3$ is hydroxy.

5. A compound according to claim 1, wherein R$^1$ and R$^2$ are ethyl.

6. A compound according to claim 5, wherein R$^3$ is a hydrogen atom.

7. A compound according to claim 5, wherein R$^3$ is hydroxy.

8. A compound having the formula:

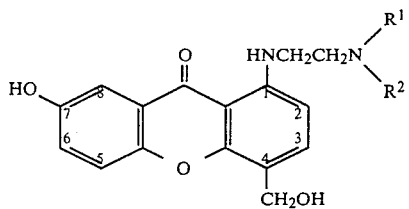

R$^1$ and R$^2$ are individually selected from one of, methyl and ethyl.

9. A compound according to claim 9, wherein R$^1$ and R$^2$ are methyl.

10. A compound according to claim 9, wherein R$^1$ and R$^2$ are ethyl.

11. A process for preparing the compound of claim 1 wherein R$^1$ and R$^2$ are methyl and R$^3$ is OH, comprising:
(a) mixing 5-methoxythiosalicylic acid with m-chloroiodobenzene under conditions to form 3-chloro-2-carboxy-4-methoxydiphenylsulfide;
(b) mixing the diphenylsulfide with polyphosphoric acid under conditions to form mixed 1-chloro-7-methoxythioxanthenones;
(c) mixing the mixed thioxanthenones with dimethylaminoethylamine and pyridine under conditions to form 1-(2-dimethylaminoethylamino)-7-methoxythioxanthenone;
(d) mixing the product of step (c) with HI under conditions to form 1-(2-dimethylaminoethylamino)-7-hydroxythioxanthenone;
(e) mixing the product of step (d) with pyridine and p-toluenesulfonyl chloride under conditions to form 1-(2-dimethylaminoethylamino)-7-toluenesulfonoxythioxanthenone;
(f) mixing the product of step (e) with formaldehyde and HOAc under conditions to form a residue;
(g) using an eluant to elute the compound; and (h) hydrolyse the toluensulfonoxy esters to the desired product.

12. A process for preparing the compounds of claim 1 wherein $R^1$ and $R^2$ and ethyl and $R^3$ is OH, comprising:
   (a) mixing 5-methoxythiosalicylic acid with m-chloroiodobenzene under conditions to form 3-chloro-2-carboxy-4-methoxydiphenylsulfide;
   (b) mixing the diphenylsulfide with polyphosphoric acid under conditions to form mixed 1-chloro-7-methoxythioxanthenones;
   (c) mixing the mixed thioxanthenones with diethylaminoethylamine and pyridine under conditions to form 1-(2-diethylaminoethylamino)-7-methoxythioxanthenone;
   (d) mixing the product of step (c) with HI under conditions to form 1-(2-diethylaminoethylamino)-7-hydroxythioxanthenone;
   (e) mixing the product of step (d) with pyridine and p-toluenesulfonyl chloride under conditions for form 1-(2-diethylaminoethylamino)-7-toluenesulfonoxythioxanthenone;
   (f) mixing the product of step (e) with formaldehyde and HOAc under conditions to form a residue;
   (g) using an eluant to elute the compound; and
   (h) hydrolyse the toluensulfonoxy esters to the desired product.

13. A process of preparing the compound of claim 1 wherein $R^1$ and $R^2$ are methyl or ethyl and $R^3$ is H, comprising:
   (a) converting 5-methoxyanthranilic acid to the corresponding diazonium salt by treatment with nitrous acid followed by addition of sodium disulfide to give the corresponding dithiosalicylic acid; and
   (b) converting the dithiosalicylic acid with p-chlorotoluene to give mixed isomeric thioxanthenones;
   (c) heating the further mixture with an ethylenediamine having the formula $H_2NCH_2CH_2NR^1R^2$ to give an intermediate having the formula:

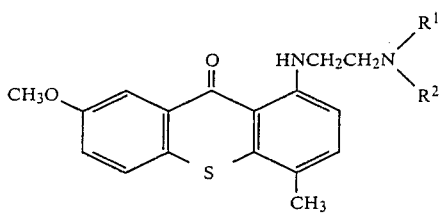

and;
   (d) heating the intermediate with a hydrohalide solution HX, where X is one of Cl, Br and I to give the product of formula:

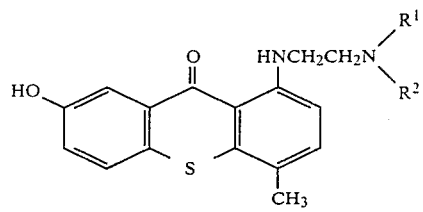

or the hydrohalide salt or other pharmaceutically acceptable salts thereof.

14. A process for preparing an intermediate for the preparation of the compound of claim 1 wherein $R^1$ and $R^2$ are methyl or ethyl and $R^3$ is OH, comprising:
   (a) combining p-methoxythiophenol with 2,6-dichlorobenzonitrile, under conditions for form 2-chloro-6-(p-methoxybenzenethio)-benzonitrile;
   (b) adding to the benzonitrile of step (a) triflouromethanesulfonic acid to form a mixture; and
   (c) adding the mixture of step (b) to water to form 1-chloro-7-methoxythioxanthenone.

15. A process according to claim 14, including treating the intermediate with N,N-dimethylethylenediamine to form 1-(2-dimethylaminoethylamino)-7-methoxy-thioxanthenone.

* * * * *